United States Patent [19]

McFarland et al.

[11] Patent Number: 4,859,052
[45] Date of Patent: Aug. 22, 1989

[54] PORTABLE SCREEN ASSEMBLY FOR VISUAL ACUITY TESTING

[75] Inventors: Diana R. McFarland; Robert P. Ginsburg; Arthur P. Ginsburg, all of Dayton, Ohio

[73] Assignee: Vistech Consultants, Inc., Beavercreek, Ohio

[21] Appl. No.: 268,629

[22] Filed: Nov. 4, 1988

Related U.S. Application Data

[63] Continuation of Ser. No. 207,464, Jun. 16, 1988, abandoned.

[51] Int. Cl.[4] .................................................. A61B 3/02
[52] U.S. Cl. ..................................... 351/239; 351/244
[58] Field of Search ............... 351/200, 201, 203, 239, 351/244, 245

[56] References Cited

U.S. PATENT DOCUMENTS 1,647,195  11/1927  Reid ..................................... 351/244

OTHER PUBLICATIONS

Teller Acuity Cards Handbook by Vistech Consultants, Inc., revised 11/86.

Primary Examiner—Rodney B. Bovernick
Assistant Examiner—P. M. Dzierzynski
Attorney, Agent, or Firm—Biebel, French & Nauman

[57] ABSTRACT

A portable screen assembly for use in combination with a series of visual acuity testing cards to test the visual acuity of an infant or otherwise functionally young (handicapped) person requiring to be held by another person comprises a three-panel screen wherein two side panels are hingedly connected to a main panel in such manner that they can be moved from folded positions overlying the back face of the main panel to positions wherein each defines a predetermined obtuse angle with the front side of the panel. A removable and collapsible brace connects the upper free corners of the side panels to hold the screen assembly in its erected position, and this brace cooperates with the main panel and a bracket of rod material to support a shield which blocks the line of view between the person holding the person under test and an opening in the main panel where successive acuity testing cards are presented to the person under test. In its erected condition, this screen assembly provides a stable and sturdy testing installation, and it is quickly and easily collapsed for storage or transportation between different locations of use.

10 Claims, 2 Drawing Sheets

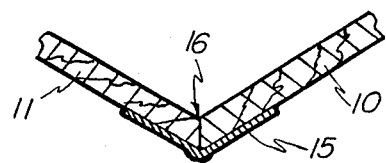
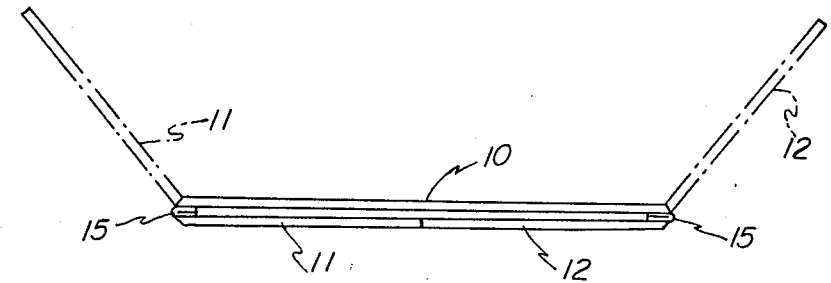
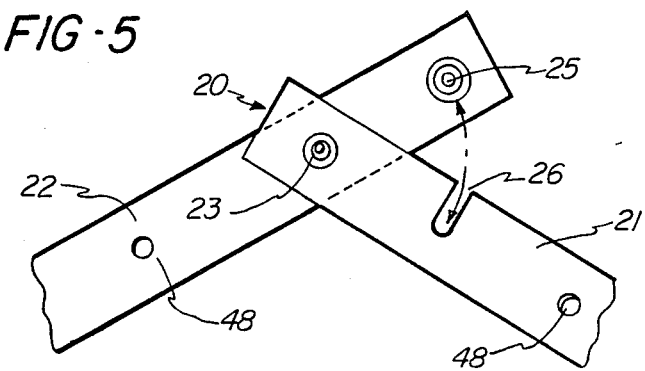
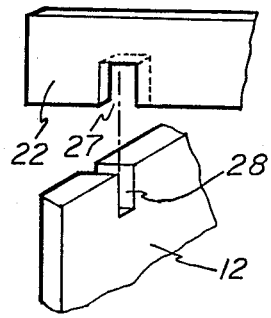
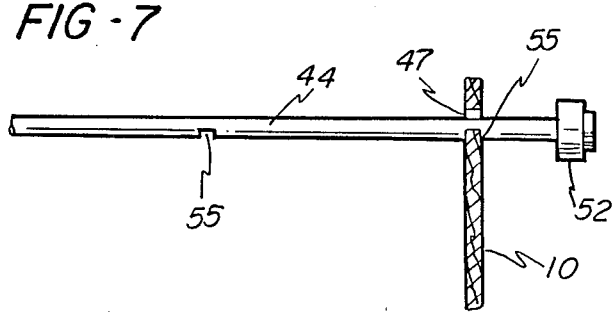

though which it is slidably engaged by a slot 29 in the strap 21. The grommet 25 includes a stem portion of smaller diameter than the grommet heads and of a length sufficient to accommodate the thickness of the strap 21, and it can slide freely along the slot 29 when the straps are being moved between their extended and collapsed positions. The straps are prevented from inadvertent collapse when in their extended position by an enlarged opening 30 at the end of the slot 29, into which the grommet head will fall when the straps are in extended position and will be retained until positively forced out of that opening by the application of pressure in the direction to cause such collapse.

PORTABLE SCREEN ASSEMBLY FOR VISUAL ACUITY TESTING

This is a continuation of co-pending application Ser. No. 207,464, filed June 16, 1988 now abandoned.

BACKGROUND OF THE INVENTION

The technology of and techniques for testing the visual acuity of infants, other young children and the functionally young (handicapped) have been the subject of considerable research over the past five to ten years, and one relatively recently developed technique known as "The Acuity Card Procedure" has been found to make it possible to estimate the visual acuity of normal infants with reasonable accuracy in a few minutes in a laboratory setting.

In testing a child by this procedure, the child sits or is held in front of a screen containing a test card having thereon a black and white grating and a blank target of the same space-average luminance as the grating. The child is shown a number of presentations of gratings of different spatial frequencies, with the left-right location of the grating varied from one presentation to the next. The observer judges the visual acuity of the child by noting the eye and head movements of the child in response to each presented test card, through a peephole in the card.

In the preferred practice of the acuity card procedure, the person holding the child is shielded from the position where each of the successive cards is presented in order to prevent such person from consciously or unconsciously influencing the child's reactions to the cards. For this purpose, provision may be made to locate a shield between the eyes of that person and the position of card presentation.

BRIEF SUMMARY OF THE INVENTION

The primary purpose of the present invention is to provide a screen assembly for infant vision testing by the acuity card procedure which will have substantial advantages of structure and convenience of use over prior devices used for this purpose, and which in addition will be readily portable in a knocked-down condition while at the same time being quick and simple to assemble for use.

The primary element of the screen assembly of the invention is a three-panel screen comprising a main panel and two side panels which are hingedly connected in such manner that the side panels can be moved from folded positions overlying the back face of the main panel to positions wherein each defines a predetermined obtuse angle with the front side of the main panel.

A removable and collapsible brace connects the upper free corners of the side panels to hold the screen assembly against accidental collapse. The assembly is completed by a U-shaped bracket of rod material which has its legs inserted through matching holes in the brace and the main panel, and the central portion of this member serves as a support for a shield which blocks the line of view from the person holding the child under test to an opening in the main panel where successive acuity testing cards are presented to the child.

The screen assembly of the invention can be set up or collapsed in not more than about a minute. When it is set up, it provides a stable and sturdy testing installation, and when it is collapsed, it is quickly and easily stored between locations of use.

BRIEF DESCRIPTION OF THE DRAWINGS

FIG. 3 is an enlarged fragmentary section on the line 3—3 of FIG. 1;

FIG. 4 shows the three-panel screen of the assembly of FIGS. 1 and 2 in collapsed condition;

FIG. 5 is a detail view of a portion of the brace member of the assembly of the FIGS. 1 and 2;

FIG. 6 is an enlarged fragmentary exploded view illustrating the complementary slot connection between the brace member and of the side panels in FIGS. 1 and 2; and FIG. 7 is a fragmentary view taken on the line 7—7 of FIG. 1.

DESCRIPTION OF THE PREFERRED EMBODIMENT

Figure 1:
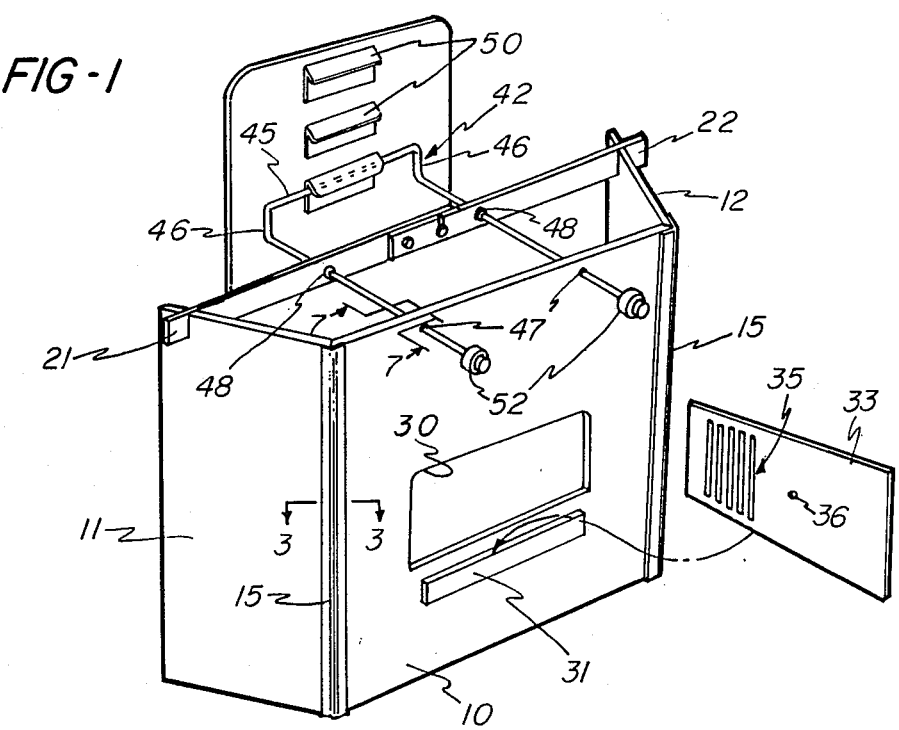
FIG. 1 is an exploded perspective view illustrating a portable screen assembly in accordance with the invention as viewed at an angle from the back thereof.

The main structural component of the portable screen assembly of the invention is a three-panel screen comprising the main panel 10 and side panels 11 and 12, all of which are preferably made from rigid board material of sufficient thickness to be self-supporting, e.g. plywood ¼ inch in thickness. The two side panels are hingedly connected to the opposite edges of the main panel 10 by means of hinge strips 15 which are bonded to adjacent edge portions of the back sides of the panels and are made of a material of such flexibility, e.g. expanded closed cell PVC, that the side panels can be folded into directly overlying relation with the back surface of the main panel. As an example of satisfactory dimensions, all three of the panels may be 32 inches high, the panels 11 and 12 may be 15 inches wide, and the panel 10 may be 30 inches wide.

Each side panel 11 and 12 can also be folded to a position wherein it defines an obtuse angle with the front surface of the main panel 10. This angle is established by appropriate beveling of one or both of the adjacent edges of the respective panels to serve as stops, as shown at 16 in FIG. 3, an angle of approximately 135° having been found to be satisfactory. When both side panels are swung forward to their advanced positions, the resulting three-panel screen will stand firmly on any flat surface, and it is held in that position by a brace assembly 20, as now described.

More specifically, the brace assembly 20 comprises a pair of rigid metal straps 21 and 22 which are pivotally connected to each other by a rivet or grommet 23 located adjacent the end of the strap 21 but at a position spaced from the corresponding end of the strap 22. The straps 21 and 22 can therefore be swung about their pivotal connection into overlying relation as part of the disassembly of the screen assembly for storage or carrying.

When the straps 21 and 22 are swung about pivotal connection 23 from their collapsed condition, they reach an extended length approximately equal to the distance between the outer edges of the panels 11 and 12 in their erected positions. They are releasably held in that position by a rivet or grommet 25 set in the strap 22 between the pivot 23 and the adjacent end of strap 22 and fitting into a slot 26 in the strap 21.

Each of these straps 21-22 is also provided adjacent its free end with a slot 27 which extends approximately one-half the width of the strap and provides an interlocking relation between the strap and a complementary slot 28 in the upper edge of the panel 11 or 12 adjacent the outer corner thereof. As shown in FIG. 6, the slots 27 and 28 are complementarily beveled so that the brace 20 provides a firm but removable interconnection between the outer portions of the panels 11 and 12 to hold them in their erected positions with respect to the main panel 10.

Figure 2:
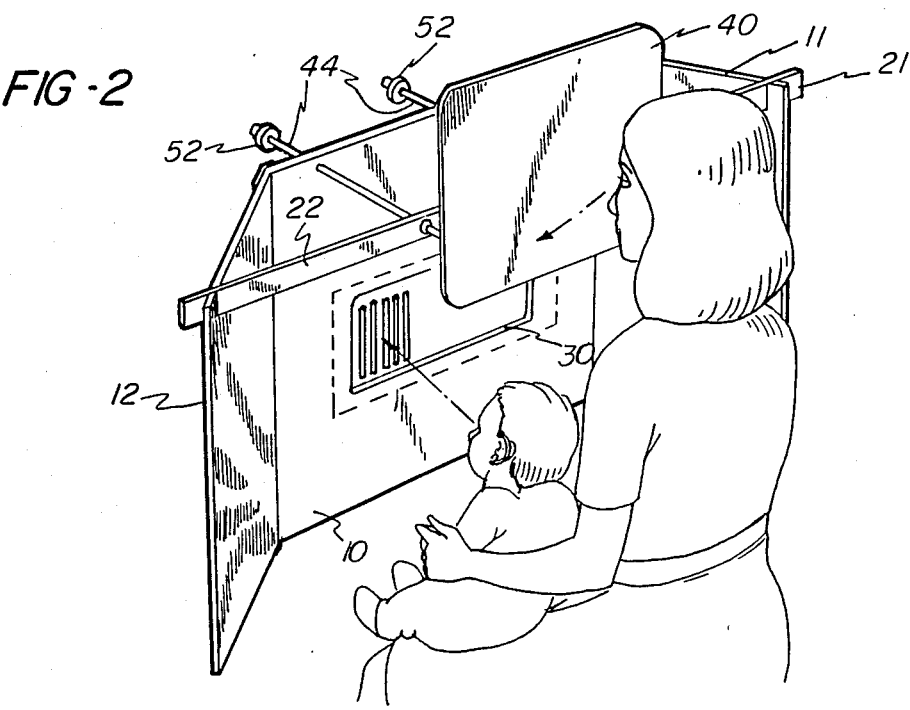
FIG. 2 is a perspective view illustrating the use of the assembly of FIG. 1 as viewed at an angle from the front side thereof.

The main panel 10 is also provided with an extended opening 30 therethrough which defines the viewing position for the acuity cards, and a support 31, such as a strip of plywood of the same thickness as the panels, is secured on the back side of the panel 10 just below the opening 30 to form a ledge for supporting each of the successive cards which are manually held in overlying relation with the opening 30. An example of such a card 33 is shown in FIGS. 1 and 2. As illustrated, the grating pattern 35 is balanced by a blank space of approximately equal area, so that the card 33 can be placed in viewing position with its pattern 35 on either side of its vertical center. The peephole 36 through which the testing person observes the child's relation to each card is at the center of the card.

A shield 40 is supported on the screen assembly at a selected height wherein it will block the line of sight between the person holding the child being tested and the viewing opening 30. The shield 40 is a rectangular panel of stiff material, e.g. plastic ⅛ inch in thickness, and it is supported at a vertically and horizontally adjustable position by means of a bracket 42 of steel rod material bent to generally U-shape to provide a pair of legs 44 and a central portion 45 connected with the legs 44 by short intermediate portions 46 bent at right angles to the legs 44.

Bracket 42 is mounted on the screen assembly by inserting its legs 44 through two pairs of aligned holes 47-48 in the main panel 10 and brace 20. The shield 40 has a plurality of extended hook-like brackets 50 secured on its back surface in spaced relation so that any one of these brackets 50 can be hung on the central portion 45 of the bracket 42 with the intermediate bracket portions 46 bracing the shield 40 against swinging movement. Preferably the exposed ends of the bracket legs 44 are provided with removable rubber tips 52 to protect the observer who is holding successive cards 33 on the support 31 and watching the child through the peephole in each card.

The plurality of hook brackets 50 provides for variation of the vertical position of shield 40 depending upon the eye level of the person holding the child being tested. The position of shield 40 can also be adjusted horizontally by moving the bracket 42 back and forth in its mounting holes 47-48. As shown in FIG. 7, the bracket legs 44 are preferably provided with a series of spaced notches 55 sized to engage the edges of the holes 47 to establish predetermined positions for the shield 40 with respect to the opening 30 so that the shield 40 can be used to locate the shield at a preferred distance from the card 35, e.g. a distance o 38, 55 or 84 cm.

In use, the screen assembly may be set on the floor but preferably is set on a table for the convenience of the persons holding the shield and conducting the testing. The use is as described in the "Background" section of this specification, and is illustrated also by the figures of the child and adult in FIG. 2. It is to be understood that while the foregoing description has referred to testing a child, the testing may be of any functionally child-like (handicapped) person, and if such person does not have to be supported in position for testing, the child 40 need not be used.

For optimum effectiveness, all of the screen panels and the shield 40 should be painted the same value of grey as the blank portions of the cards 33, in order to avoid possible visual distraction of the person under test. The same objective is contributed to by the overall construction of the screen assembly of the invention, which avoids any gap or other visual interruption of the monochromatic background provided for the test cards, thereby assuring that the only distraction to which the child under test can respond will be the pattern 35 on each test card.

While the form of apparatus herein described constitutes a preferred embodiment of the invention, it is to be understood that the invention is not limited to this precise form of apparatus and that changes may be made therein without departing from the scope of the invention.

What is claimed is:

1. A portable screen assembly for use in combination with a visual acuity testing card to test the visual acuity of a person located in a predetermined testing position, comprising:
    (a) a main panel having front and back sides and having an opening therethrough,
    (b) a pair of sides panels hingedly connected to the opposite side edges of said main panel whereby each said side panel is movable to a position defining a predetermined obtuse angle with the front side of said main panel so that said three panels constitute a free standing screen facing said testing position,
    (c) a brace member,
    (d) means for movably connecting the opposite ends of said brace member to the upper free corners of said side panels to hold said side panels in said fixed angular relation with said main panel, and
    (e) means on said back side of said main panel for supporting a visual acuity test card for viewing from the opposite side of said screen through said opening.

2. A portable screen assembly as defined in claim 1 wherein said brace comprises a pair of rigid members having a pivotal connection therebetween providing for movement of said members into side-by-side relation facilitating portability of said assembly, and means for releasably securing said members together in the position where each extends in the opposite direction from said pivotal connection therebetween.

3. A portable screen assembly as defined in claim 1 which is particularly adapted for testing a person requiring to be held in said testing position by another person and which further comprises an opaque shield separate from said screen, and bracket means for supporting said shield on said screen in position to block the line of sight between said opening and the person holding the person being tested.

4. A portable screen assembly as defined in claim 3 wherein said bracket means comprises a U-shaped member of rod material, and means defining two pairs of aligned openings in said main panel and said brace for receiving and supporting the legs of said U-shaped member in horizontally extending positions.

5. A portable screen assembly as defined in claim 4 wherein said legs of said bracket means include longitudinally spaced notches for engagement with the wall of said main panel surrounding said holes therein to establish predetermined positions of said shield with respect to said opening.

6. A portable screen assembly as defined in claim 4 further characterized in that said shield includes a plurality of inverted hook members adapted for engagement over the central portion of said U-shaped member to support said shield at a corresponding plurality of selected heights.

7. A portable screen assembly as defined in claim 1 wherein said panels are formed of stiff board material, and each of said side panels is hingedly connected to said main panel by a flexible hinge strip secured to the back sides of said panels to provide for folding movement of each of said side panels into overlapping relation with said back side of said main panel for ready carrying or storage.

8. A portable screen assembly as defined in claim 7 wherein at least one of the side edges of said main panel and each of said side panels is beveled to provide a stop limiting relative hinged movement of said panels toward said front side of said main panel to establish said obtuse angular relation between said side panels and said main panel.

9. A portable screen assembly for use in combination with a visual acuity testing card to test the visual acuity of a person located in a predetermined testing position, comprising:
 (a) a main panel formed of stiff board material having front and back sides and having an opening therethrough,
 (b) a pair of side panels of stiff board material connected by hinge means to the opposite side edges of said main panel,
 (c) said hinge means comprising a flexible hinge strip secured to adjacent portions of the back sides of said panels to provide for folding movement of each of said side panels into overlapping relation with said back side of said main panel for ready carrying or storage,
 (d) means limiting hinged movement of said side panels away from said back side of said main panel to positions wherein each of said side panels defines a predetermined obtuse angle with the front side of said main panel so that said three panels constitute a free standing screen facing said testing position,
 (e) a brace member,
 (f) means for movably connecting the opposite ends of said brace member to the upper free corners of said side panels to hold said side panels in said fixed angular relation with said main panel, and
 (g) means on said back side of said main panel for supporting a visual acuity test card for viewing from the front side of said screen.

10. A portable screen assembly as defined in claim 9 which is particularly adapted for testing a person requiring to be held in said testing position by another person and which further comprises:
 (a) an opaque shield separate from said screen,
 (b) a U-shaped member of rod material,
 (c) means defining two pairs of aligned openings in said main panel and said brace for receiving and supporting the legs of said U-shaped member in horizontally extending positions, and
 (d) at least one inverted hook member on said shield adapted for engagement over the central portion of said U-shaped member to support said shield in position to block the line of sight between said opening in said main panel and the person holding the person being tested.

* * * * *